US00PP29042P3

(12) United States Plant Patent
Kordes

(10) Patent No.: US PP29,042 P3
(45) Date of Patent: Mar. 6, 2018

(54) MINIATURE ROSE PLANT NAMED 'KORPOT064'

(50) Latin Name: *Rosa hybrida*
Varietal Denomination: KORpot064

(71) Applicant: W. Kordes Söhne Rosenschulen GmbH & Co. KG, Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Offenseth-Sparrieshoop (DE)

( * ) Notice: Subject to any disclaimer, the term of this patent is extended or adjusted under 35 U.S.C. 154(b) by 23 days.

(21) Appl. No.: 14/998,641

(22) Filed: Jan. 25, 2016

(65) Prior Publication Data

US 2017/0215310 P1 Jul. 27, 2017

(51) Int. Cl.
*A01H 5/02* (2006.01)

(52) U.S. Cl.
USPC ..... Plt./121

(58) Field of Classification Search
USPC ..... Plt./121
See application file for complete search history.

*Primary Examiner* — Keith O Robinson
(74) *Attorney, Agent, or Firm* — Samuel R. McCoy, Jr.

(57) ABSTRACT

'KORpot064' is a new and distinct variety of *Rosa hybrida* which is characterized by the combination of a compact and upright growth habit, dark green and glossy foliage, very good resistance to *Botrytis* and powdery mildew, deep pink very-double flowers, and very good shelf life as a pot plant. The new variety propagates successfully by stem cuttings and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORpot064'.

BACKGROUND OF THE INVENTION

Parentage: The *Rosa hybrida* variety 'KORpot064' is the result of a controlled cross-pollination breeding program carried out by the inventor in Offenseth-Sparrieshoop, Germany. The objective of the said breeding program was to create a new and distinct rose plant with unique qualities, such as:

1. Uniform growth and flowering;
2. Abundant attractive pink colored recurrent flowers;
3. Attractive and abundant foliage; and
4. Excellent shelf life for the plant when grown as a commercial pot rose.

This combination of qualities is not present in prior rose cultivars known to the inventor. These objectives have been substantially achieved and in that distinguish 'KORpot064' from all other varieties known to the inventor.

'KORpot064' is a seedling selection which resulted from the controlled pollination of an unnamed *Rosa hybrida* female breeding line developed and owned by the same inventor, the seed parent, and *Rosa hybrida* 'RUId244a' (not patented), the pollen parent, during the summer of 2011. As part of a rose development program, Tim-Hermann Kordes germinated seeds from the aforementioned hybridization during the following winter and conducted evaluations and observations on the resulting seedlings in a controlled environment in Offenseth-Sparrieshoop, Germany. The resulting seedlings exhibited distinctive physical and biological characteristics. The new rose plant was selected as a single plant in April of 2012 from the seedling beds due to its superior characteristics and asexually propagated for further evaluation. This new and distinctive rose variety was given the name 'KORpot064'.

Asexual Reproduction: The first asexual propagation of 'KORpot064' was performed in June of 2012 at the inventor's nursery in Offenseth-Sparrieshoop, Germany. Subsequently, 'KORpot064' has been successfully propagated by stem cuttings in Jackson County, Oreg. These initial and other subsequent propagations conducted in controlled environments demonstrate that 'KORpot064' reproduces true to type in successive generations of asexual reproduction.

SUMMARY OF THE INVENTION

The following characteristics have been repeatedly observed and represent the distinguishing characteristics of the new *Rosa hybrida* cultivar 'KORpot064'. These traits, in combination, distinguish 'KORpot064' as a new and distinct cultivar.

1. *Rosa hybrida* 'KORpot064' exhibits a compact, upright growth habit; and
2. *Rosa hybrida* 'KORpot064' exhibits dark green and glossy foliage; and
3. *Rosa hybrida* 'KORpot064' exhibits very good resistance to *Botrytis* and powdery mildew; and
4. *Rosa hybrida* 'KORpot064' exhibits a very double petal count; and
5. *Rosa hybrida* 'KORpot064' exhibits a medium flower size for a miniature rose; and
6. *Rosa hybrida* 'KORpot064' exhibits very good shelf life as a pot plant; and
7. *Rosa hybrida* 'KORpot064' exhibits deep pink flowers, at anthesis.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot064', taken from twelve month old plants.

DETAILED BOTANICAL DESCRIPTION

The following is a detailed botanical description of a new and distinct variety of *Rosa hybrida* known as 'KORpot064', based upon field observations made in July of 2015, from twelve month old container-grown plants in a greenhouse environment in Jackson County, Oreg. Those skilled in the art will appreciate that certain characteristics will vary with older or, conversely, with younger plants. 'KORpot064' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORpot064' and comparisons with other varieties of *Rosa hybrida* are provided below.

General plant description:

*Growth rate*.—Moderately vigorous.

*Growth habit*.—Compact and upright.

*Mature dimensions*.—25 to 30 cm tall and 20 cm wide, on average, when grown as a 10 cm nursery pot.

*Cold hardiness*.—Unknown.

*Propagation*.—Stem cuttings.

*Disease resistance*.—Very good resistance to *Botrytis* (*Botrytis cinerea*), powdery mildew (*Sphaerotheca pannosa*) and downy mildew (*Peronospora sparsa*) in a greenhouse environment in Jackson County, Oreg.

Root system: Fibrous.

Stems:

*Stem color*.—Young stems are Yellow-Green Group 144A; mature stems are Yellow-Green Group 146A.

*Anthocyanin intonations*.—Greyed-Red Group 181A intonations are present on new growth.

*Stem surface texture*.—Both immature and mature stems exhibit a smooth texture.

*Stem dimensions*.—Typical mature stems are approximately 20 to 25 cm long and 3 to 4 mm in diameter.

*Prickles*.—Incidence — Present; 10 prickles per 10 cm of stem, on average. Size — Average length is 3 mm. Immature prickle color — Yellow-Green Group 145C. Mature prickle color — Yellow-Green Group 145C and senescing to Greyed-Orange Group 177B. Anthocyanin intonations — None present. Shape — Linear. Texture — Smooth.

Leaves:

*Arrangement*.—Imparipinnate compound leaves; mature axillary leaves consisting of 5 leaflets.

*Attachment*.—Petiolate.

*Dimensions*.—70 to 80 mm long and 55 to 60 mm wide, on average.

*Abundance*.—Average; approximately 50 to 60 leaves per plant.

*Stipules*.—Size — 10 mm long and 4 mm wide. Stipule color — Green Group 137A. Anthocyanin intonations — None. Stipitate glands — Abundant on the margins. Margins — Glandular toothed. Texture, adaxial surfaces — Smooth with fine white hairs. Texture, abaxial surfaces — Glabrous. Apex — Apiculate. Base — Winged.

*Petiole*.—Length — Average 15 mm. Diameter — Average 1.5 mm. Petiole color, adaxial and abaxial surfaces — Yellow-Green Group 144A. Margins — Entire with a limited number of stipitate glands. Anthocyanin intonations — Greyed-Red Group 182A on stipitate glands and occasionally on the adaxial midrib surface. Prickles — None. Stipitate glands — Limited number; present on the margins. Texture — Smooth, with abundant fine white hairs, White Group 155C. Strength — Somewhat strong.

*Rachis*.—Length — Average 13 mm. Diameter — Average 1 mm. Color — Green Group 137A on the upper surface and Yellow-Green Group 144A on the lower surface. Anthocyanin intonations — Greyed-Red Group 182A on margins. Margins — Entire. Prickles — A few small prickles on some leaves. Stipitate glands — Limited number present along margins and underneath. Pubescence — Abundant fine white hairs, White Group 155C, on the upper surface. Texture — Upper surface is smooth; papillate underneath.

*Leaflets*.—Quantity — Normally 5 leaflets on normal leaves in middle of the stem. Dimensions — Average size of the terminal leaflet is 35 mm long and 21 mm wide. Shape — Ovate. Apex — Acuminate. Base — Obtuse. Margins — Serrated; no undulation. Luster and texture, adaxial surface — Semi-glossy and smooth. Luster and texture, abaxial surface — Matte and leathery. Juvenile foliage color, adaxial surface — Yellow-Green Group 144A. Juvenile foliage color, abaxial surface — Yellow-Green Group 144A. Mature foliage color, adaxial surface — Green Group 137A. Mature foliage color, abaxial surface — Yellow-Green Group 147B. Anthocyanin intonations — Greyed-Red Group 182A along margins of juvenile leaflets. Venation — Reticulate. Petiolule — Dimensions — 1 to 2 mm long and 1 mm in diameter. Petiolule color, adaxial surface — Green Group 137A. Petiolule color, abaxial surface — Yellow-Green Group 144A with intonations of Greyed-Red Group 182A. Prickles — None present. Texture, adaxial and abaxial surfaces — Smooth. Margins — Entire, with limited number of fine hairs and stipitate glands on both the adaxial and abaxial surfaces.

Inflorescence:

*Inflorescence type*.—Typically solitary flowers; occasionally multiple flowers arranged in corymbs. Flowers are held upright.

*Blooming habit*.—Recurrent.

*Quantity of flowers*.—Generally three to four flower buds per corymb.

*Size*.—80 mm tall and 80 mm wide, on average.

*Peduncle of corymb*.—Length — 10 mm average length. Diameter — 2 to 3 mm average diameter. Color — Yellow-Green Group 146A. Anthocyanin intonations — None. Strength — Strong. Texture — Smooth with a limited number of stipitate glands. Pubescence — Pubescent; fine white hairs, White Group 155C.

Flowering laterals: Present below the initiation of inflorescence. Generally 1 to 2 flowering laterals are present, with 2 to 4 flowers per flowering shoot.

Bud:

*Bud form*.—Long; pointed ovoid.

*Size*.—Upon opening, 20 to 30 mm in length from base of receptacle to distal end of bud and 15 mm diameter at its widest point.

*Texture*.—Smooth.

*Color, as sepals first unfold*.—Red-Purple Group N66B.

*Color when one-quarter open, inner side*.—Marginal zone — Red-Purple Group N66C. Middle zone — Red-Purple Group N66C. Basal zone — Green-White Group 157D.

*Color when one-quarter open, outer side*.—Marginal zone — Red-Purple Group N66B. Middle zone — Red-Purple Group N66B. Basal zone — Green-White Group 157D.

Flower:

*Pedicels, solitary flowers and flowers of corymbs*.—Surface — Glabrous with an abundance of stipitate glands are present. Length — 20 to 35 mm, on average. Diameter — 2 to 3 mm, on average. Color — Yellow-Green Group 144C. Anthocyanin intonations — Greyed-Purple Group 178C on stipitate glands only. Strength — Somewhat strong. Texture — Papillate.

*Calyx*.—General — Comprised of five polysepalous sepals, with weak foliaceous appendages present on three of the five sepals. Diameter of calyx — 50 mm, at anthesis. Sepals — Color, adaxial surface — Yellow-Green Group 144A. Color, abaxial surface — Yellow-Green Group 147C. Anthocyanin intonations — Greyed-Purple Group 178C is present only on stipitate glands. Size — 20 to 30 mm long and 7 mm wide, on average. Apex — Both cirrose and apiculate apices observed. Base — Flat at union with receptacle. Quantity — Five. Texture, adaxial surface — Hoary. Texture, abaxial surface — Papillate. Margins — Cilliate. Stipitate glands — Limited to abundant on the abaxial surface.

*Corolla*.—General shape of corolla — Round; rosette. Shape of corolla when viewed from the side — Upon opening, upper portion — Flattened convex. Upon opening, lower portion — Flattened convex. Open flower, upper portion — Flattened convex. Open flower, lower portion — Flat. Dimensions — Medium for a miniature rose. When open, the average flower diameter is 50 to 55 mm and the average flower height is 20 mm. Fragrance — None. Duration — On the plant 18 to 24 days. Senesced petals clinging. Petals — Petal count — Exhibits very double flowers with approximately 50 petals under normal conditions. Petal arrangement — Formal. Petal reflex — Innermost petals are somewhat; outermost petals are strongly reflexed; occasionally doubly reflexed. Timing of petal reflex — One-by-one. Petal margin — Entire; innermost petals are somewhat ruffled. Petal shape — Obovate; some of the innermost petals are irregular. Apex — Acute. Base — Cuneate. Dimensions — 14 to 20 mm long and 6 to 20 mm wide. Texture, inner surface — Smooth. Texture, outer surface — Smooth. Petal color, upon opening — Outermost petals, inner surface — Marginal zone — Red-Purple Group N66C. Middle zone — Red-Purple Group N66D. Basal zone — Green-White Group 157A. Outermost petals, outer surface — Marginal zone — Red-Purple Group N66C, with intonations of Red-Purple Group N66D. Middle zone — Red-Purple Group N66C, with intonations of Red-Purple Group N66D. Basal zone — Green-White Group 157A. Innermost petals, inner surface — Marginal zone — Red-Purple Group 58C. Middle zone — Red-Purple Group 58D. Basal zone — Yellow Group 2A. Innermost petals, outer surface — Marginal zone — Red-Purple Group 58C, with intonations of Yellow Group 4C on the midrib. Middle zone — Red-Purple Group 58C, with intonations of Yellow Group 4C on the midrib. Basal zone — Yellow Group 2B. Basal petal spots, upon opening — No distinct coloration at the petal base. Petal color, after opening — Outermost petals, inner surface — Marginal zone — Red-Purple Group 65A. Middle zone — Red-Purple Group 65B. Basal zone — White Group 155A. Outermost petals, outer surface — Marginal zone — Red-Purple Group 68B, with intonations of White Group 155C. Middle zone — Red-Purple Group 68B, with intonations of White Group 155C. Basal zone — White Group 155C. Innermost petals, inner surface — Marginal zone — Red-Purple Group N66C. Middle zone — Red-Purple Group N66D. Basal zone — White Group 155C. Innermost petals, outer surface — Marginal zone — Red-Purple Group N66C, with intonations of White Group 155C. Middle zone — Red-Purple Group N66C, with intonations of White Group 155C. Basal zone — White Group 155C. Basal petal spots, after opening — No distinct coloration at the petal base. General Tonality — On open flower, Red-Purple Group 62A. No change in the general tonality at the end of the tenth day. Afterwards, general tonality is Red-Purple 62D. Petaloids — Quantity — 20 petaloids per flower, on average. Dimensions — Approximately 3 to 15 mm long and 2 to 5 mm wide. Color, inner surface — Marginal zone — Red-Purple Group N66D. Middle zone — Red-Purple Group N66D. Basal zone — White Group 155A. Color, outer surface — Marginal zone — Red-Purple Group N66B with intonations of White Group 155A on the midrib. Middle zone — Red-Purple Group N66C with intonations of White Group 155A on the midrib. Basal zone — White Group 155A. Margins — Undulated. Shape — Spatulate; many petaloids are highly irregular. Apex — Obtuse. Base — Attenuate. Texture, inner and outer surfaces — Smooth.

Reproductive organs:

*Stamens*.—Quantity — Approximately 50, on average, and regularly arranged around the styles. Anthers — Shape — Reniform. Dimensions — 1.5 to 2 mm long and 1 mm wide, on average. Color — Yellow-Orange Group 16B. Pollen — Scarce. Pollen color — Greyed Orange Group 164C. Filaments — Color — Green-Yellow Group 1B. Length — 3 to 4 mm.

*Pistils*.—Quantity — Average; approximately 60. Stigmas — Dimensions — 0.5 mm long and 0.5 mm wide. Location — Superior in position to anthers. Color — Greyed-Yellow Group 162D. Styles — Length — Approximately 7 mm long. Color — Yellow-Green Group 145D, with intonations of Red-Purple Group N66A.

*Ovary*.—Dimensions — 2 mm long and 1.5 mm in diameter. Color — Yellow-Green Group 145D.

*Receptacle*.—Shape — Funnel-shaped; occasionally urn-shaped. Dimensions — Approximately 4 to 5 mm high and 6 to 7 mm wide. Surface texture and pubescence — Smooth, slightly glaucous and pubescent; abundance of fine white hairs. Color — Yellow-Green Group 144B.

Hips and seed formation: Not observed.

COMPARISONS WITH THE PARENTS

The new rose plant may be distinguished from its seed parent, an unnamed female breeding line, by the following combination of characteristics:

1. 'KORpot064' exhibits a deep pink general tonality of the flower, whereas the seed parent exhibits a cherry red general tonality of the flower.
2. 'KORpot064' exhibits a medium flower size for a miniature rose, whereas the seed parent exhibits a large flower for a miniature rose.
3. 'KORpot064' exhibits a very-double flower petal count, whereas the seed parent exhibits a semi-double flower petal count.

The new rose plant may be distinguished from its pollen parent, *Rosa hybrida* 'RUId244a', by the following combination of characteristics:

1. 'KORpot064' exhibits a deep pink general tonality of the flower, whereas 'RUId244a' exhibits a soft pink general tonality of the flower.
2. 'KORpot064' exhibits a mostly solitaire flowers, whereas 'RUId244a' exhibits flowers in small clusters.
3. 'KORpot064' exhibits very good shelf life as a pot plant, whereas 'RUId244a' exhibits average shelf life as a pot plant.

COMPARISON WITH THE MOST SIMILAR *ROSA* CULTIVAR KNOWN TO THE INVENTOR

For a comparison, several physical characteristics of the rose variety 'KORcarubo' (not patented), a rose variety from the same inventor are compared to 'KORpot064' in Chart 1.

CHART 1

| Characteristic | 'KORpot064' | 'KORcarubo' |
|---|---|---|
| General tonality of the flower. | Red-Purple Group 62A. | Red-Purple Group 58C. |
| Average diameter of the corolla, at anthesis. | 50 to 55 mm. | 50 mm. |
| Flower petal count. | 50. | 30 to 40. |

That which is claimed is:

1. A new and distinct variety of rose plant named 'KORpot064', as described and illustrated herein.

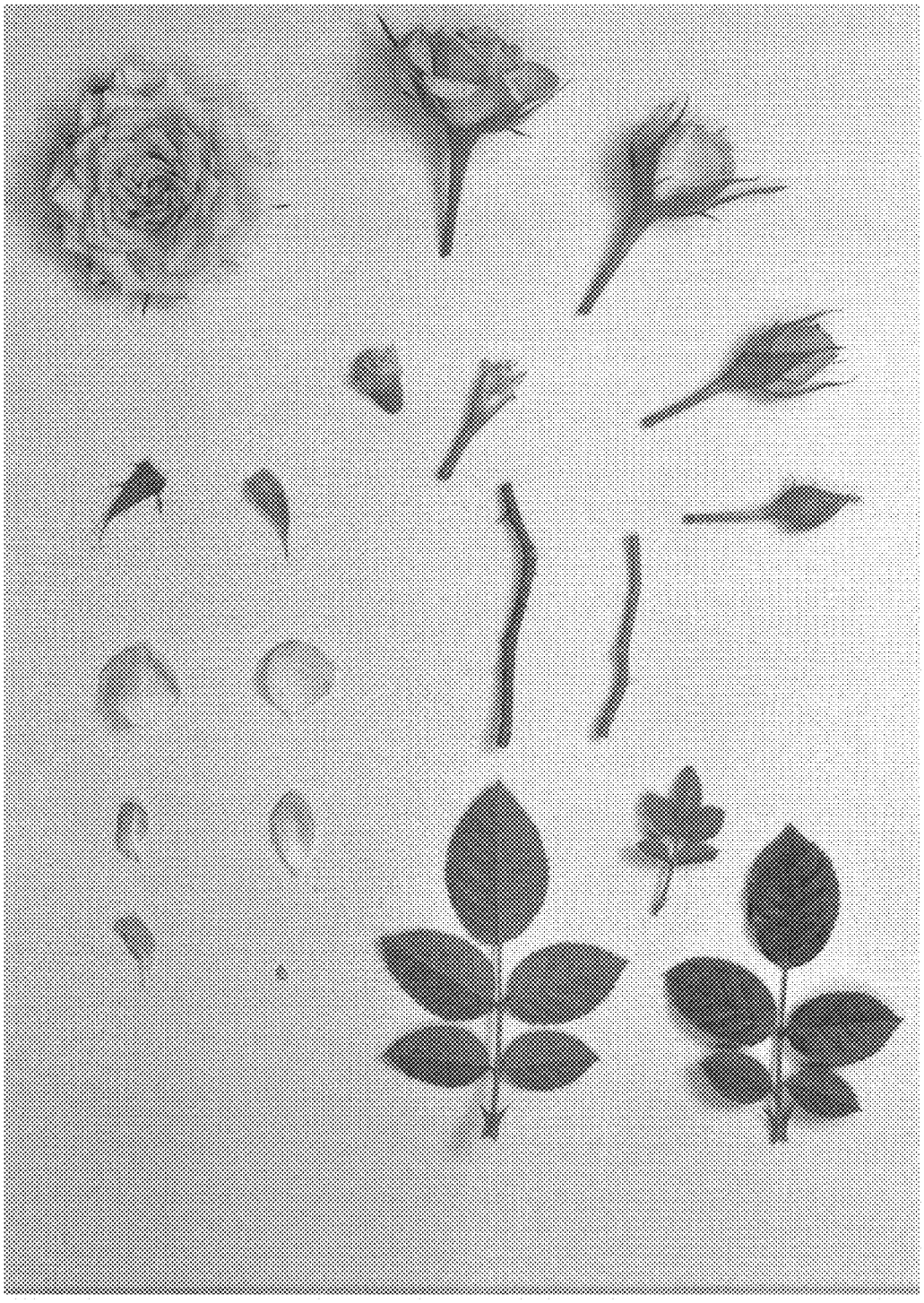

* * * * *